United States Patent
Pereira Quaresma et al.

(10) Patent No.: US 9,149,208 B2
(45) Date of Patent: Oct. 6, 2015

(54) DEVICE FOR ASSESSING THE SPINAL COLUMN

(75) Inventors: Claudia Regina Pereira Quaresma, Lisbon (PT); Mário António Bastro Forjaz Secca, Miraflores (PT); Filipe Oliveira Dos Santos, São Domingos de Rana (PT)

(73) Assignee: UNIVERSIDADE NOVA DE LISBOA, Lisbon (PT)

( * ) Notice: Subject to any disclaimer, the term of this patent is extended or adjusted under 35 U.S.C. 154(b) by 0 days.

(21) Appl. No.: 12/920,450

(22) PCT Filed: Mar. 6, 2009

(86) PCT No.: PCT/IB2009/005018
§ 371 (c)(1),
(2), (4) Date: Aug. 31, 2010

(87) PCT Pub. No.: WO2009/109859
PCT Pub. Date: Sep. 11, 2009

(65) Prior Publication Data
US 2011/0004125 A1    Jan. 6, 2011

(30) Foreign Application Priority Data
Mar. 7, 2008 (PT) .......................... 103990

(51) Int. Cl.
*A61B 5/107* (2006.01)
*A61B 5/00* (2006.01)

(52) U.S. Cl.
CPC ............. *A61B 5/1077* (2013.01); *A61B 5/4561* (2013.01)

(58) Field of Classification Search
USPC .................. 33/514.2, 515; 600/594, 595; 300/514.2, 515
See application file for complete search history.

(56) References Cited

U.S. PATENT DOCUMENTS

| | | | |
|---|---|---|---|
| 2,295,447 | A | 9/1942 | Bierman |
| 4,425,713 | A | 1/1984 | Rotella |

(Continued)

FOREIGN PATENT DOCUMENTS

| | | |
|---|---|---|
| DE | 19833568 A1 | 2/2000 |
| FR | 1051065 A | 1/1954 |
| FR | 2661600 A1 | 11/1991 |

OTHER PUBLICATIONS

Claudia Quaresma et al.; "Development of a Mechanical Instrument to Evaluate Biomechanically the Spinal Column in Pregnant Women"; Proceedings of the International Conference on Biomedical Electronics and Devices, Insticc PR, Portugal; Jan. 1, 2009; pp. 310-313, XP008112966.

(Continued)

*Primary Examiner* — Sean Dougherty
(74) *Attorney, Agent, or Firm* — John P. White; Cooper & Dunham LLP

(57) ABSTRACT

A device for assessing the spinal column intends to assess the lateral curvatures and deviations in the spinal column, in a standing position. It can be a non-invasive instrument that allows reproducing the position of each vertebra in the spinal column, from the first cervical vertebra to the first sacral vertebra. The device can include or consist of two parts: a first part designated as body and a second part defined as support. The first part can include or can consist of a vertical piece (that fits in the support) and several horizontal pieces. Each horizontal piece will touch the spinal crest of each vertebra in the spinal column, from the first cervical vertebra to the first sacral vertebra. The support can include or can consist of two pieces: a vertical piece, wherein the instrument's body vertical piece is fitted and a base whereon the feet of the patient under assessment are placed.

8 Claims, 6 Drawing Sheets

(56) References Cited

U.S. PATENT DOCUMENTS

| | | | |
|---|---|---|---|
| 4,444,204 A * | 4/1984 | Bryant et al. | 600/594 |
| 5,012,819 A * | 5/1991 | Marras et al. | 600/594 |
| 5,471,995 A * | 12/1995 | Halliday | 600/594 |
| 5,582,186 A | 12/1996 | Wiegand | |
| 6,468,233 B2 * | 10/2002 | Cook | 600/594 |
| 6,907,672 B2 * | 6/2005 | Said | 33/552 |
| 2002/0049393 A1 | 4/2002 | Cook | |
| 2003/0220590 A1 | 11/2003 | Csonka | |

OTHER PUBLICATIONS

International Search Report for PCT/IB2009/005018 dated Feb. 10, 2010.

Neusa Maria Costa Alexandre et al., "Modelo de Avaliação Físico-Funcional da Coluna Vertebral", Rev Latino-am Enfermagem, Mar. 2001, p. 67-75.

Lee, Yung-Hui et al., "Regrssionally determined vertebral inclination angles of the lumbar spine in static lifts", Clinical Biomechanics, vol. 15, 2000, p. 672-677.

Harlick, Joanne C. et al., "Palpation identification of spinous processes in the lumbar spine", Manual Therapy, Dec. 2007, p. 56-62.

Hinman, Martha R., "Comparison of thoracic kyphosis and postural stiffness in younger and older women", The Spine Journal, Apr. 2004, p. 413-417.

Norton, Barbara J. et al., "Reliability and Concurrent Validity of the Metrecom for Length Measurements on Inanimate Objects", Physical Therapy, vol. 73, No. 41, Apr. 1933, p. 266-274.

Fa, Teixeira et al., "Confiabilidade e Validade das Medidas da Cifose Torácica Através do Método Flexicurva", Rev. bras. fisioter., São Carlos, maio/jun. 2007, vol. 11, No. 3, p. 199-204.

Harisson, Deed E. et al., "Sagittal Skin Contour of the Cervical Spine: Interexaminer and Intraexaminer Reliability of the Flexicurve Instrument", Journal of Manipulative and Physiological Therapeutics, Sep. 2005, vol. 28, No. 7, pp. 516-519.

Walsh, M. et al., "Reliability and validity of the Metrecom Skeletal Analysis System in the assessment of sagittal plane lumbar angles", Clinical Biomechanics, 1995, vol. 10, No. 4, pp. 222-223.

* cited by examiner

DEVICE FOR ASSESSING THE SPINAL COLUMN

This application is a U.S. national phase filing under 35 U.S.C. §371 of PCT Application No. PCT/IB2009/005018, filed Mar. 6, 2009, and claims priority under 35 U.S.C. §119 to Portuguese patent application no. 103990, filed Mar. 7, 2008, the entireties of both of which are incorporated by reference herein.

TECHNICAL FIELD

This disclosure relates to a device for assessing the spinal column.

BACKGROUND

The incidence of backache-related problems is quite frequent and common such that it should be studied as an epidemic and social disease (Knoplich, 2003). Some authors state that backache can result in greater absence at the workplace, thus increasing an expense overload in health systems.

Vertebral algiae are a relevant problem in modern society (Alexandre & Moraes, 2001). Thus, in order to better understand this problem instruments are necessary which provide an overall assessment of the spinal column.

There are many devices for assessing the spinal column, such as x-ray, computerized axial tomography and magnetic resonance. However, few might be considered as non-invasive or as capable of analyzing the spinal column in a standing position. Some of these later devices are: the flexible ruler; "Metrecom Skeletal Analysis System."

The x-ray is the most commonly used invasive instrument for assessing the spinal column and it is the most employed method when intending to validate other instruments aiming to assess the spinal column (Harlick and al, 2007; Crazy-Giroux et. al, 2006).

The objective of the product intended to protect would have to assess lateral curvatures and deviations in the spinal column, in a standing position. It would have to be a non-invasive instrument that would allow the position of each vertebra to be reproduced, by identifying each spinal crest in the spinal column, from the first cervical vertebra to the first sacral vertebra. So being, we would have a complete and accurate assessment of the entire spinal column.

The existing non-invasive methods assess the curvatures in the spinal column and the movement of some segments in this structure. Some of those instruments, which will be hereinafter described, served as a reference for carrying out the product that we intend to protect.

One of those methods for assessing the curvatures in the spinal column is based on the collection of images through filming. These images will constantly have to be analyzed by means of image software. Lee and Chen (2000) used this methodology to assess the behavior of the lumbar and sacral column while performing some activities.

One of the reference products in the construction of the present instrument was the Flexible Ruler. Harrison et. al (2005), Hinman (2004), Teixeira and Carvalho (2007) are some of many authors that used the Flexible Ruler. It is a non invasive instrument that assesses the curvatures in the spinal column, in a standing position.

The Flexicurve method consists of the following steps: the Flexible Ruler is first positioned in the articulation wherein the assessment is desired to start and it is molded to the spinal column up to the articulation wherein the assessment is desired to end. Subsequently to being removed from the patient's spinal column, the Flexible Ruler is then placed on graph paper, wherein the outline thereof is carried out.

Another non-invasive instrument, which also assesses the curvatures in the spinal column, is the Metrecom Skeletal Analysis System being a non-validated product and which was used by Walsh and Breen (1995). The Metrecom Skeletal Analysis System consists of an electromechanical scanner that, subsequently to contacting each vertebra in the spinal column and transferring such that data to a particular computer software, identifies the previously-mentioned bone structure alignment (Norton, (1993).

The product "Electro-mechanical assembly for measurements of spinal column curvatures" referred to in US2003220590 assesses curvatures in a certain segment of the spinal column. It consists of a backpack and several sensors incorporated in an adjacent section of the patient's spinal column. Those sensors will determine the curvatures in the column in a standing position and under dynamic circumstances.

Another product for assessing curvatures in the spinal column in a standing position is the "Posture analyzer" disclosed in US2002049393. It consists of: a panel wherein a spinal column is drawn presenting curvatures which are considered as those normal for a human being; a part designated "pen" that will determine the position of each vertebra; a base where two feet are drawn.

In the case of this device, the patient will have to place both feet in the defined position which is drawn on the base. The patient will have his/her back facing the panel where a spinal column presenting normal curvature dimensions is drawn. A part designated as "pen" is attached to the panel which is movable in horizontal and vertical directions and which will travel the spinal column in the vertebrae anterior-posterior position, thus defining the curvatures in the spinal column.

The product disclosed in U.S. Pat. No. 4,425,713 is defined by its author as an instrument that assesses posture. According to its author it assesses lordosis, ciphosis and scoliosis. This device consists of a vertical piece comprising: 15 horizontal pieces that have assessed the anterior-posterior position of the spinal column; a horizontal piece that will be placed at the vertex of the patient's head; two horizontal pieces assessing the shoulder girdle position; two horizontal pieces assessing the pelvic girdle position. The product further consists of a base where two feet are drawn. The patient will have to place both feet on those which are drawn on the base of the product.

All aforesaid instruments have been used as basis for the development and construction of the product that we intended to protect.

After this research we realized that there is no device with the following features.

BRIEF SUMMARY

This disclosure describes a device to assess lateral curvatures and deviations in the spinal column, in a standing position. It is a non-invasive instrument that allows the position of each vertebra in the spinal column to be reproduced, from the first cervical vertebra to the first sacral vertebra.

Subsequently, the preparation and production of the measuring apparatus for lateral deviations and curvatures of the spinal column under loading situation took place.

This elaboration firstly consists of a non-detailed overall drawing of the apparatus based on some of the instruments previously described, so as to define de apparatus measurements, thus two parallel studies being performed:

Subsequently, the mechanism details for each piece were defined. Afterwards, several pieces were produced in order to accomplish the necessary adjustments.

By building this non-invasive product we expect to contribute for a better identification of spinal column dysfunctions in the human being in a standing position. And, by means of a more accurate diagnosis, programs might be implemented and performed for more directly intervening in each patient's specific problem.

DETAILED DESCRIPTION OF THE INVENTION

This device consists of two parts: a first part designated as body and a second part defined as support.

The first part consists of a vertical piece (that fits in the support) and several horizontal pieces. The vertical piece consists of a ratchet which is attached to a profile, four bars and two support plates on top of these two first structures, wherein the inferior structure also allows fitting in the support. The connection between the two plates and between the ratchet and the profile is made by two spigots. Each of these horizontal pieces contact the spinal crests of each vertebra in the spinal column and serve as position indicators, from the first cervical vertebra to the first sacral vertebra. Such contact is made by means of a ratchet coupled to two pinions disposed horizontally on a piece with an integral rod. This piece abuts against another piece connecting with the vertical piece of the instrument's body. Such interface is made by means of the bars and ratchet by four openings and a pinion respectively. A milled screw with an horizontal U-shape foil guarantees the attachment of the horizontal piece of the instrument's body in the vertical piece of the same.

The support is composed by two pieces: a base abutting on four feet where the person under assessment places the feet and a vertical piece, wherein the vertical piece of the instrument's body fits. The later is composed of a rectangular base profile that supports the instrument's body weight and a horizontal plate with four openings for the connection between the body and the instrument's support.

Figure 1:
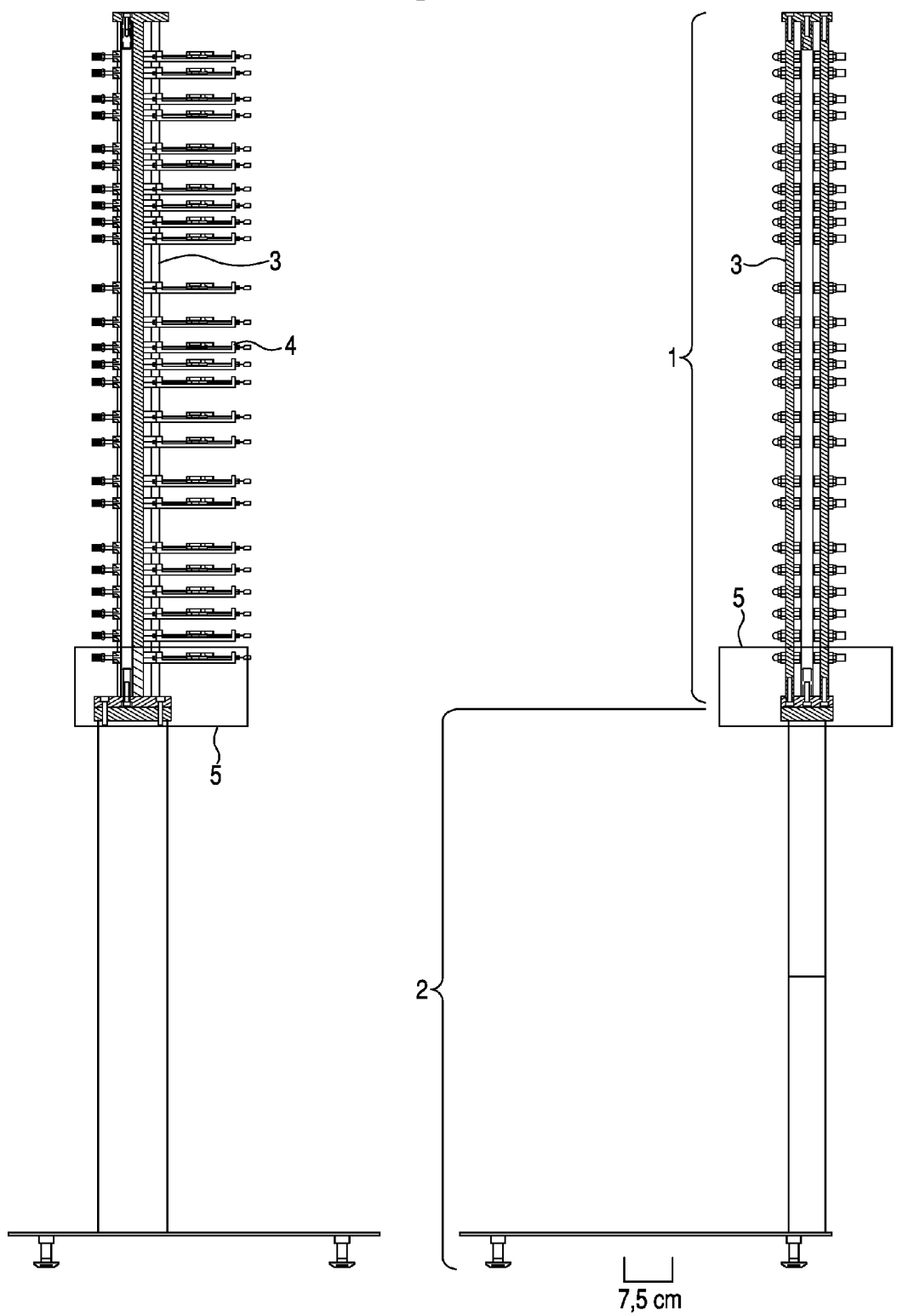
FIG. 1 shows two partial cross-section views of the entire instrument.
Figure 2:
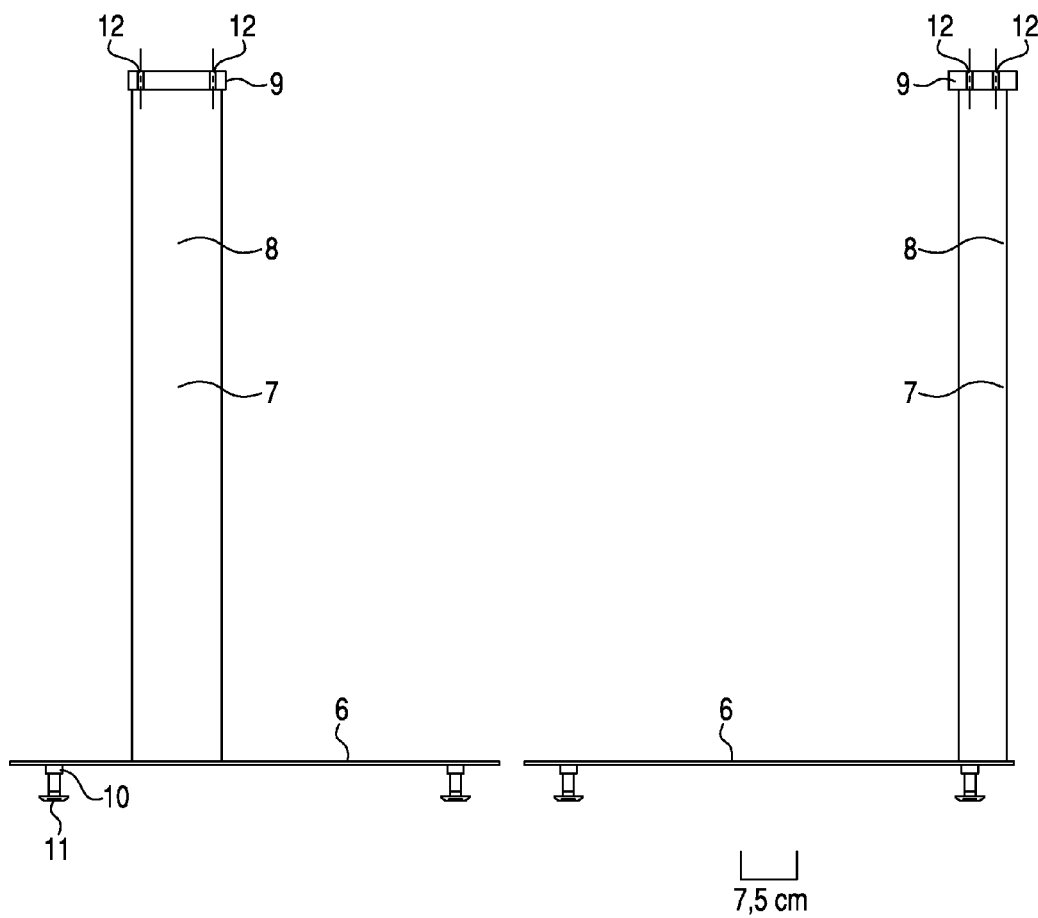
FIG. 2 shows two views of the instrument's support with identification of the horizontal and vertical pieces.
Figure 3:
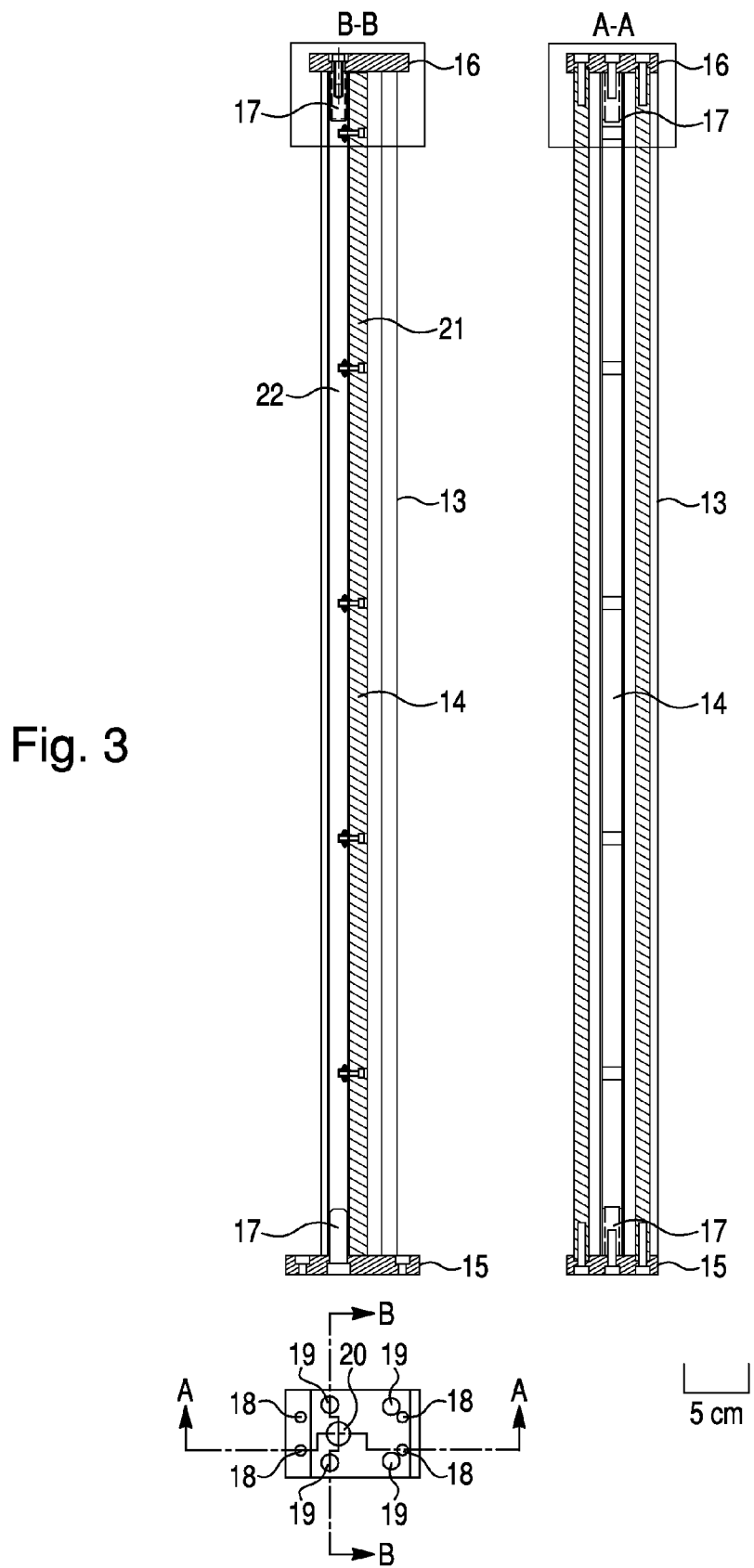
FIG. 3 shows three views of the instrument's body.

The present invention will be now explained in detail, reference being made to the enclosed drawings, in which:

FIG. 1 shows two partial cross-section views of the entire instrument. The view on the left enhances the represented attachment between the body and the instrument's support. The view on the right represents the attachment among the rods of the instrument's body. Both views show a frame surrounding the attachments;

FIG. 2 shows two views of the instrument's support with identification of the horizontal and vertical pieces;

FIG. 3 shows three views of the instrument's body. The plan view shows the cuts represented in the other views. The cut B-B represents in further detail the ratchet attached to a profile and the attachment thereof to two support plates by means of two spigots inserted in the profile. Cut A-A represents in more detail the bars and attachment thereof and still a further view of the profile with the attachment spigots. The vertical piece consists of a ratchet attached to a profile, four bars and still two support plates on top of these two structures, wherein the inferior plate also allows fitting in the support. The connection between the two plates and between the ratchet and profile is made by two spigots.

Figure 4:
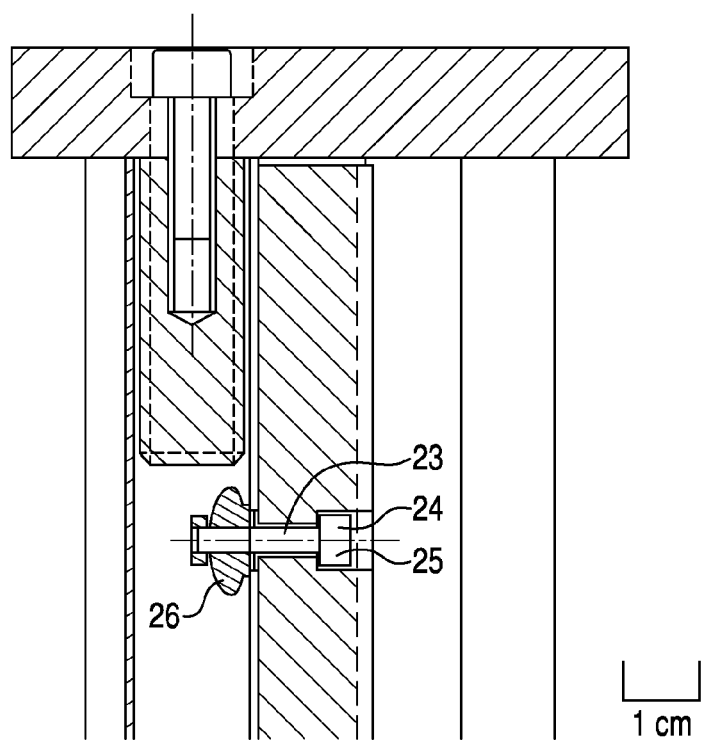
FIG. 4 shows an enlargement of the top of the instrument's body.
Figure 5:
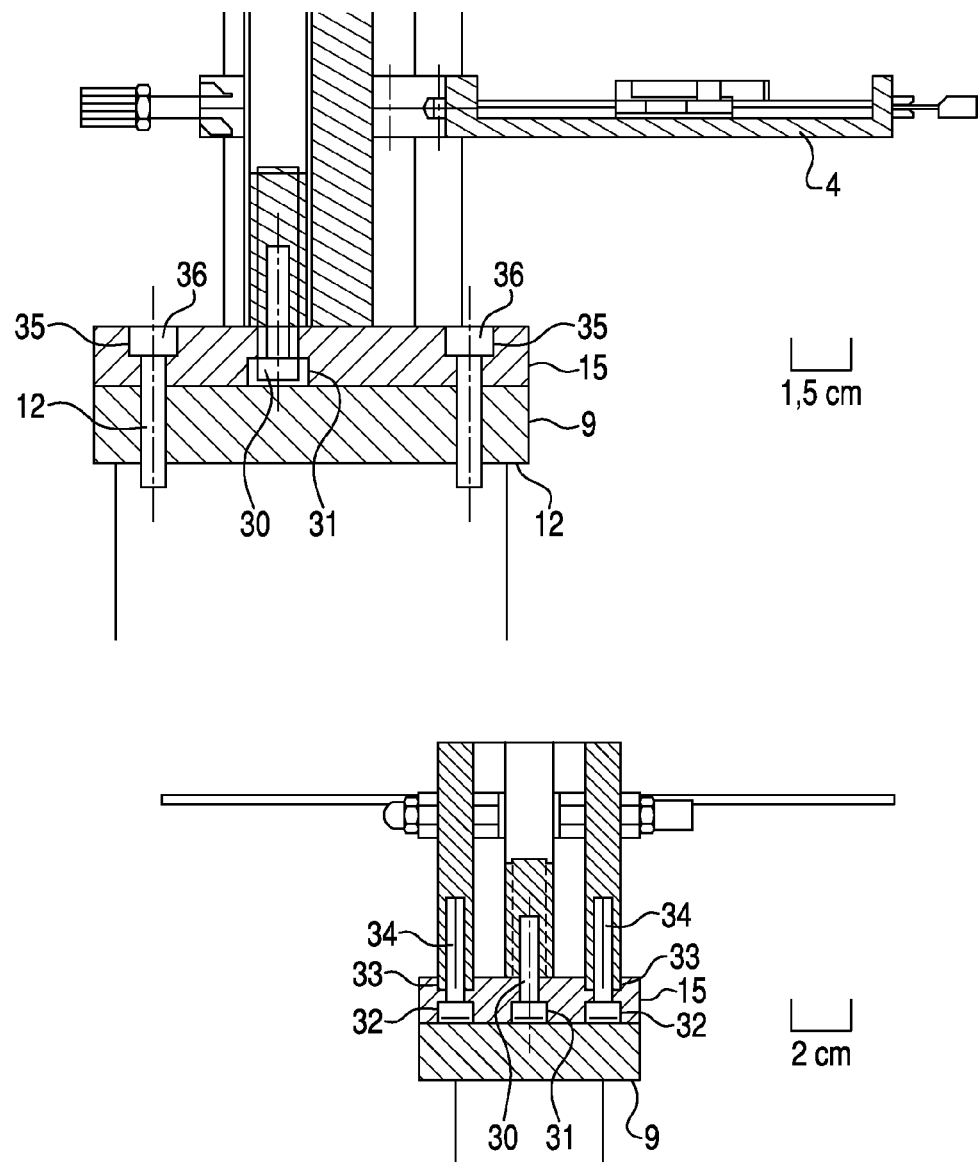
FIG. 5 shows an enlargement of the attachments
Figure 6:
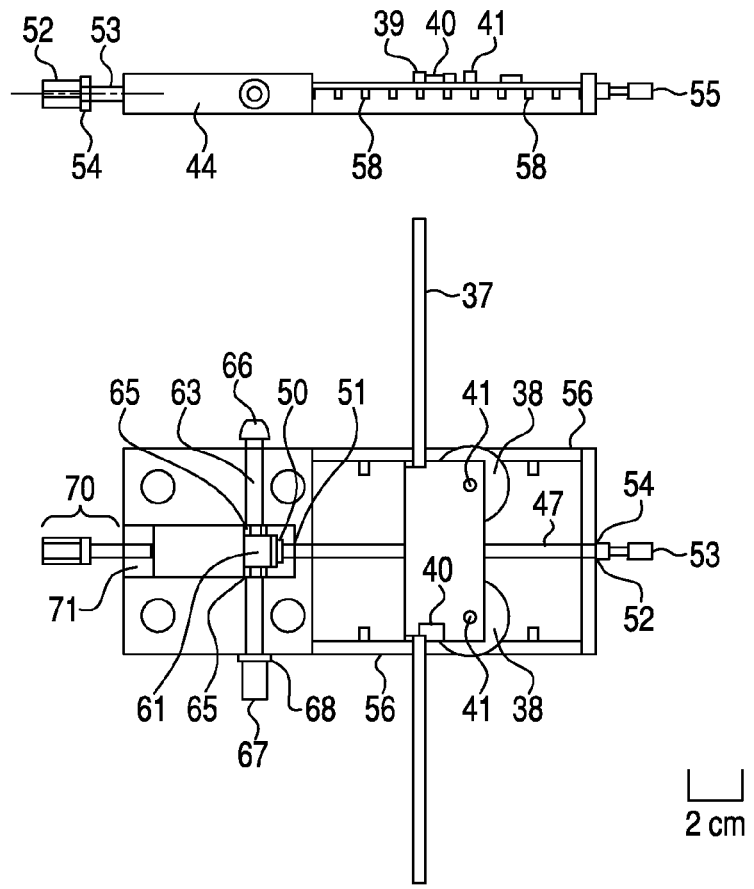
FIG. 6 shows three views of the horizontal pieces of the instrument's body.

FIG. 4 shows an enlargement of the top of the instrument's body represented with frames in FIG. 3;

FIG. 5 shows an enlargement of the attachments represented with frames in FIG. 1;

FIG. 6 shows three views of the horizontal pieces of the instrument's body. In the top view the pinion can be seen operating as interface with the ratchet. This pinion is attached, through two nuts, to a thread rod with a handle in one end thereof. The four openings are also shown allowing the horizontal pieces of the instrument's body to pass through the bars.

Figure 7:
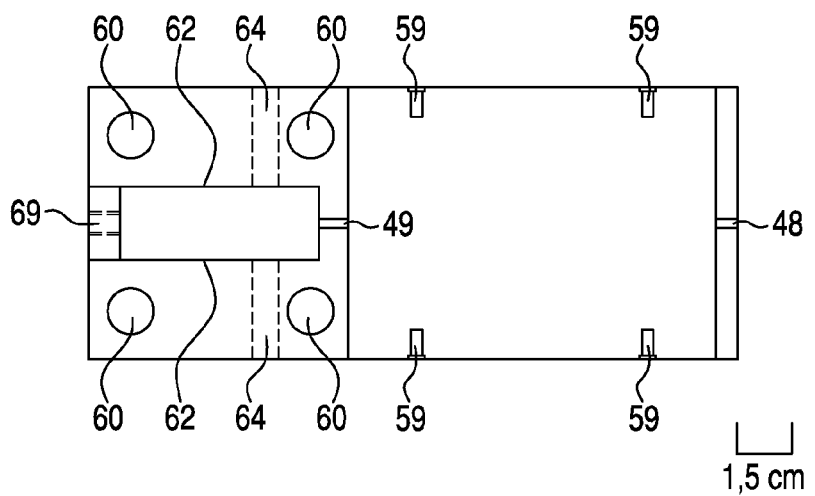
FIG. 7 shows two views of a piece of the horizontal piece of the vertebra body.

Furthermore, the horizontal ratchet and the two pinions can also be observed on the support piece thereof with a thread rod. The later is attached in the ends thereof by nuts and shows a handle in the farthest end from the bars' passageway. In the three views a screw and a small U-shape plate can be seen;

FIG. 7 shows two views of a piece of the horizontal piece of the vertebra body.

Reference being made to the drawings, FIG. 1 shows the instrument identifying two main pieces (1 and 2) and two frames (5) around the interface and attachment thereof. FIG. 4 shows an enlargement of the elements within those frames. FIG. 2 shows the piece 2 in FIG. 1 divided into pieces 6 and 7. The patient under assessment places both feet on piece 6. The later abuts against four pieces 10, each comprising a tongue thread M6 on the upper end thereof and being linked by the respective nut 9 which is welded at the bottom face of piece 6. The interface and support of piece 1 on piece 2 are made by means of piece 7 through piece 8 and profile 9 respectively. The piece 8 has four openings (12) with a thread groove M6 being the openings responsible for the said attachment.

The piece 1 in FIG. 1 consists of piece 3 and piece 4 in FIG. 1. The later is represented in FIG. 3. It consists of four pieces 13 and one piece 14.

The piece 14 consists of the ratchet 21 and profile 22. Both are drilled in five points. In ratchet 21, this opening (23) has a box (24) so that the head of the screw (25) remains below the recess line (below the teeth). This screw M6 (DIN 912) will be screwed in a nut (26) nailed in profile 23.

Each piece 13 has a groove M6 thread opening (27) in each upper and lower face, wherein the screw (28) shall be screwed passing through pieces 15 and 16.

The two pieces 17 inserted in profile 22 direct piece 14 into position which together with the pieces 13 is attached to the two pieces 15 and 16. The pieces 17 have a thread M6 opening (29) similarly to pieces 13 with a screw (30) also passing through 15 and 16. Those two pieces have several openings with boxes represented by 18, 19 and 20 in FIG. 3.

The openings 20 are wide relatively to the screws M6 under use (similar to the ones previously described) and have an oval box (31) for the screw head (30) in order to allow adjusting the position of piece 14. They exist in piece 15 with the box in the lower face and in the piece 16 with the box in the upper face.

The openings 19 have the typical tolerance for the passing of screws (34) similarly to the ones described above. Each one of them comprises two boxes: one box (32) housing the screw head and another box (33) housing the end of piece 13. In piece 15, the box 32 is placed at the lower face and box 33 is placed at the upper face. In opposition, piece 16 comprises the box 32 at the upper face and box 33 at the lower face.

The holes 18 exist mainly in piece 15, since they outline the connection interface between the body and the instrument's support, together with openings 12 of piece 9 in FIG. 2. The later receives screws (36) which pass through piece 15. In this, the box (35) for each screw is placed in the upper face thereof.

All boxes and screws are represented in FIGS. 4 and 5.

One of the plural position indicators, piece 4, in FIG. 1 is represented in FIG. 6. In this figure pinions 38 and ratchet 37 are depicted. The later has a funnel form at its end being the contact point with the person under assessment. The movement is actuated by pinions 38 and the position of the ratchet 37 determines one of the position coordinates of the point intended to determine. These three pieces are supported by piece 39 and they are attached on the upper side by slab 40 and two screws M3(41) embossed therein. The later are screwed in two thread openings M3, passing through the rotation axis of pinions 38 and along a small vertical tube (42) that maintains the position thereof. The ratchet 37 besides being delimited by pinions and slab 40, is also delimited by a wall (43) of piece 39, allowing the first to move mainly in the traction direction which is imposed by the pinions 36. The piece 39 abuts against piece 44 and has an opening (45), transverse to the length thereof, the central third being threaded M3 (46). The thread rod M3 (47) passes through such opening and is retained in piece 44. It passes through holes 48 and 49 and is attached in the most medial end by a cap nut 50 and a bush 51, serving as a cover, and in the most lateral end thereof by a nut system (52)/counter-nut (53) and a bush (54). In such end there is further a small handle (55) glued to the rod. The rotation of the handle promotes the rotation of the thread rod 47, serving as an integral rod of piece 4, that, being attached at its ends, actuates the movement on piece 39. This piece is laterally delimited sidelong by the two profiles 56 that fit in two areas of piece 39 which are lowered (57) and maintain the position thereof in the normal directions to the rotation axis of the thread rod, or integral rod. These profiles are attached to piece 44 by means of four screws M3 (58) built-in in the profiles, the piece 44 having four thread openings M3 (59). The first has a scale which allows defining the position of piece 39, which in its turn allows determining a further coordinate for the position of the point intended to define. Finally, the third coordinate is obtained by moving piece 3 over piece 4, both in FIG. 1, such being made by the passage of the piece 44 through pieces 13 in FIG. 3 through openings 60 in FIG. 7 and by the pinion roll 61 in FIG. 6 on ratchet 14 and along box 62 in FIG. 3. This pinion is in a thread rod M6 (63), inserted in opening 64of piece 44 and being attached by two nuts 60 screwed therein. Both are lowered in height and width such that they do not contact the teeth in ratchet 14. This rod has a cap nut 66, serving as a cover, at one end and a milled nut 67 at the other end which is attached to the counter-nut 68 (screwed together) acting as a handle and controlling the movement at the vertical axis.

When screwed in the thread opening M6 (69) of piece 44, the pressure of piece 70 on the slab 71, both illustrated in FIG. 6, against the piece 14 in FIG. 3 guarantees retaining the position of piece 3 on piece 4, both illustrated in FIG. 1.

The piece 70 is similar to the handle referred to above, consisting of a milled nut 72 screwed in a thread rod M6 (73) and against a counter-nut 74.

DESCRIPTION OF OPERATION

The product allows assessing dysfunctions or pathologies in the spinal column, as well as the efficiency degree of rehabilitation programs.

It can be applied in any population and situations, including children, adolescents, pregnant women, adults and seniors. It is a product that can be used by health care credential professionals.

BIBLIOGRAPHY

Harrison et al (2005) *Sagittal skin contour of the cervical spine: interexaminer and intra examiner reability of the Flexicurve instrument*. Journal of Manipulative and Physiological Therapeutics. Vol 28, 7; 516-519

Harlick, J. Milosavljevic, S. (2007) *Palpation identification of spinus processes in the lumbar spine*. Manual Therapy 12, 56-62

Hinman, M. (2004) *Comparison of thoracic kiphosis and postural stiffness in younger and older women*. Spine Journal 4; 413-417.

Norton, B J; Ellison, J B. (1993) *Reliability and concurrent validity of the Metrecom for length measurements on inanimate*. Phys. Ther. 73; 266-274.

Teixeira, F A; Caravalho, G A(2007) *Confiabilidade e validade das medidas da cifose torácica através do Método Flexicurva [Reliability and validity of thoracic kiphosis measurement through Flexicurve Method]*. Revista Brasileira de Fisioterapia. Vol.11, 3; 199-204.

Pinel-Giroux, F.; Mac-Thiong, J.; Guise, J.; Labelle, H. (2006) *Computerized assessment of sagittal curvatures of spine—Comparison between Cobb and tangent circles techiques*. J. Spinal Disord. Tech, vol. 19,7;507-512.

Walsh and Breen (1995) *Reability and validity of the Metrecom Skeletal Analysis in the assessment of sagittal plane lumbar angles*. Clinical Biomechanics vol. 10 no. 4; 222-223.

Walsh et al (2007) *Three-dimensional motion analysis of the lumbar spine during "Free Squat" weight lift training*. American Journal of Sports Medicine, vol 35, 6; 927-932.

The invention claimed is:

1. A device for providing a non-invasive assessment of lateral curvatures, deviations, and a position of each vertebra from a first cervical vertebra to a first sacral vertebra in a spinal column of a person in a standing position, the device comprising:
   a support including,
      a base on which a person under the assessment stands; and
      a vertical support having a top and a bottom, the bottom being attached to the base;
   a vertical body attached to the top of the vertical support; and
   a plurality of position indicators attached horizontally to the vertical body, each ore of the plurality of position indicators further comprising:
      a handle portion fixed on the vertical body; and
      an integral rod abutting against the handle portion, the integral rod configured to make contact with a spinal crest of a vertebra from the first cervical vertebra to the first sacral vertebra via a horizontal ratchet coupled. to two pinions disposed on the integral rod, the integral rod having a scale indicating a position of each vertebra;
   wherein the vertical body includes a cap enclosing a profile attached to a vertical ratchet embedded within the profile, the vertical body being attached via two spigots to a top support plate at a top of the vertical body and to a bottom support plate at a bottom of the vertical body where the vertical body attaches to the vertical support;

wherein the attachment of the vertical body to the top and bottom support surfaces allows for the cap, the vertical ratchet, and the profile to be held in place and further provides for an adjustment in the position of the cap, the vertical ratchet, and the profile; and wherein the device is configured to assess the position of each vertebra, including assess a horizontal position of each vertebra and a vertical position of each vertebra from the first cervical vertebra to the first sacral vertebra, wherein the device is configured to assess the horizontal position by reading a position of each vertebra from the scale and assess the vertical position by a vertical movement of each one of the plurality of position indicators wherein the vertical movement of each position indicator being made possible through a pinion roll located on the vertical ratchet of the vertical body.

2. The device for providing a non-invasive assessment, according to claim 1, wherein each of the plurality of position indicators includes one piece, configured to also horizontally and transversally move, that allows undertaking horizontal and anterior-posterior movements, wherein data concerning the position and deviation of each vertebrae are gathered subsequent to the placement of each of the plurality of position indicators at the level of a corresponding spinal crest.

3. A method of use of a device for providing a non-invasive assessment of lateral curvatures, deviations, and a position of each vertebra from a first cervical vertebra to a first sacral vertebra in a spinal column of person, the device comprising:

a support including,
  a base on which a person under the assessment stands; and
  a vertical support having a top bottom, the bottom being attached to the base;
  a vertical body attached to the top of the vertical support; and
  a plurality of position indicators attached horizontally to the vertical body, each one of the plurality of position indicators further comprising:
    a handle portion fixed on the vertical body; and
    an integral rod abutting against the handle portion, the integral rod configured to make contact with a spinal crest of a vertebra from the first cervical vertebra to the first sacral vertebra via a horizontal ratchet coupled to two pinions disposed on the integral rod, the integral rod having a scale indicating a position of each vertebra;

wherein the vertical body includes a cap enclosing a profile attached to a vertical ratchet embedded within the profile, the vertical body being attached via two spigots to a top support plate at a top of the vertical body and to a bottom support plate at a bottom of the vertical body where the vertical body attaches to the vertical support;

wherein the attachment of the vertical body to the top and bottom support surfaces allows for the cap, the vertical ratchet, and the profile to be held in place and further provides for an adjustment in the position of the cap, the vertical ratchet, and the profile; and wherein the device is configured to assess the position of each vertebra, including assess a horizontal position of each vertebra and a vertical position of each vertebra from the first cervical vertebra to the first sacral vertebra, wherein the device is configured to assess the horizontal position by reading a position of each vertebra from the scale and to assess the vertical position by a vertical movement of each one of the plurality of position indicators wherein the vertical movement of each position indicator being made possible through a pinion roll located on the vertical ratchet of the vertical body, wherein the device is configured to assess dysfunctions and/or pathologies in the spinal column, as well as the efficiency degree of rehabilitation programs.

4. A method of use of a device for providing a non-invasive assessment of lateral curvatures, deviations, and a position of each vertebra from a first cervical vertebra to a first sacral vertebra in a spinal column of a person, the device comprising:

a support including,
  a base on which a person under the assessment stands; and
  a vertical support having a top and a bottom, the bottom being attached to the base;
  a vertical body attached to the top of the vertical support; and
  a plurality of position indicators attached horizontally to the vertical body, each one of the plurality of position indicators further comprising:
    a handle portion fixed on the vertical body; and
    an integral rod abutting against the handle portion, the integral rod configured to make contact with a spinal crest of a vertebra from the first cervical vertebra to the first sacral vertebra via a horizontal ratchet coupled to two pinions disposed on the integral rod, the integral rod having a scale indicating a position of each vertebra;

wherein the vertical body includes a cap enclosing a profile attached to a vertical ratchet embedded within the profile, the vertical body being attached via two spigots to a top support plate at a top of the vertical body and to a bottom support plate at a bottom of the vertical body where the vertical body attaches to the vertical support;

wherein the attachment of the vertical body to the top and bottom support surfaces allows for the cap, the vertical ratchet, and the profile to be held in place and further provides for an adjustment in the position of the cap, the vertical ratchet, and the profile; and wherein the device is configured to assess the position of each vertebra, including assess of a horizontal position of each vertebra and a vertical position of each vertebra from the first cervical vertebra to the first sacral vertebra, wherein the device is configured to assess the horizontal position by reading a position of each vertebra from the scale and assess the vertical position by a vertical movement of each one of the plurality of position indicators wherein the vertical movement of each position indicator being made possible through a pinion roll located on the vertical ratchet of the vertical body, wherein each of the plurality of position indicators includes one piece, configured to also horizontally and transversally move, that allows undertaking horizontal and anterior-posterior movements, wherein data concerning the position and deviation of each vertebrae are gathered subsequent to the placement of each of the plurality of position indicators at the level of a corresponding spinal crest, wherein the device is configured to assess dysfunctions and/or pathologies in the spinal column, as well as the efficiency degree of rehabilitation programs.

5. The device of claim 1, wherein the integral rod has a funnel at one end of the rod at which contact is made with the person under the assessment.

6. The device of claim 1, wherein each handle portion includes a handle fixed to the vertical body via a nut system.

7. The device of claim 1, wherein the two pinions on the integral rod are configured to actuate a movement in a position of the horizontal ratchet, which in turn determines a position of a vertebra in contact with the integral rod.

8. The device of claim 1, wherein the device is configured to assess dysfunctions and/or pathologies in the spinal column, as well as the efficiency degree of rehabilitation programs.

\* \* \* \* \*